(12) United States Patent
Bodlovich et al.

(10) Patent No.: US 8,677,942 B2
(45) Date of Patent: Mar. 25, 2014

(54) AQUAPONICS SYSTEM

(75) Inventors: Andrew Bodlovich, Nimbin (AU); Kevin Gleeson, Goolmangar (AU)

(73) Assignee: Urban Ecological Systems Ltd., Nimbin (AU)

( * ) Notice: Subject to any disclaimer, the term of this patent is extended or adjusted under 35 U.S.C. 154(b) by 630 days.

(21) Appl. No.: 12/373,462

(22) PCT Filed: Jul. 13, 2007

(86) PCT No.: PCT/AU2007/000978
§ 371 (c)(1),
(2), (4) Date: Jan. 12, 2009

(87) PCT Pub. No.: WO2008/006172
PCT Pub. Date: Jan. 17, 2008

(65) Prior Publication Data
US 2010/0031893 A1 Feb. 11, 2010

(30) Foreign Application Priority Data
Jul. 13, 2006 (AU) ................................ 2006903780

(51) Int. Cl.
*A01K 63/04* (2006.01)
*A01G 31/00* (2006.01)
*A01K 61/00* (2006.01)

(52) U.S. Cl.
USPC ........................................ 119/227; 119/226

(58) Field of Classification Search
USPC ................... 119/227, 226, 243, 260
See application file for complete search history.

(56) References Cited

U.S. PATENT DOCUMENTS

| | | | | |
|---|---|---|---|---|
| 3,635,816 A * | 1/1972 | Golub | | 210/602 |
| 3,742,912 A * | 7/1973 | Chen et al. | | 119/51.03 |
| 5,046,451 A | 9/1991 | Inslee et al. | | |
| 5,054,424 A * | 10/1991 | Sy | | 119/260 |
| 5,081,954 A * | 1/1992 | Monus | | 119/260 |
| 5,121,708 A | 6/1992 | Nuttle | | |
| 5,544,621 A * | 8/1996 | Haurilesko | | 119/230 |
| 5,693,220 A * | 12/1997 | Sceusa | | 210/151 |
| 5,919,366 A * | 7/1999 | Cameron | | 210/602 |
| 6,065,245 A | 5/2000 | Seawright | | |
| 7,867,396 B2 * | 1/2011 | Hill | | 210/602 |

FOREIGN PATENT DOCUMENTS

| | | | | |
|---|---|---|---|---|
| DE | 240 327 A | 10/1986 | | |
| DE | 240327 A1 * | 10/1986 | ............. | A01G 31/00 |
| GB | 1533848 | 11/1978 | | |
| RU | 2028772 C1 | 2/1995 | | |

(Continued)

OTHER PUBLICATIONS

International Search Report from PCT/AU2007/000978 dated Sep. 14, 2007 (3 pages).

(Continued)

*Primary Examiner* — Kimberly Berona
(74) *Attorney, Agent, or Firm* — Osha • Liang LLP (57) ABSTRACT

The present invention relates to an aquaponics system and method. There is provided an aquaponics system including a tank (10) for housing at least one aquatic animal species; a plant growing apparatus (18) for housing one or more plant species growing in an aqueous environment; and a biofilter module including a solids removal means (12) and a biological waste digestion unit (14) including a biological species for digesting solids to produce plant nutrients. Plant nutrients are transferred to the plant growing apparatus (18) and at least a portion of the water is returned to the tank (10).

6 Claims, 5 Drawing Sheets

(56) References Cited

FOREIGN PATENT DOCUMENTS

| RU | 2078500 C1 | | 5/1997 |
|---|---|---|---|
| WO | WO 8303333 A | * | 10/1983 |
| WO | 0032540 A1 | | 6/2000 |
| WO | WO 2006005118 A2 | * | 1/2006 |

OTHER PUBLICATIONS

International Preliminary Report on Patentability from PCT/AU2007/000978 dated Jun. 26, 2008 (6 pages).
Examination Report issued in Australian Application No. 2007272317 dated Nov. 18, 2010 (3 pages).
Notice of Acceptance issued in Australian Application No. 2007272317 dated Dec. 21, 2010 (3 pages).
Wilson Andrew Lennard, "Minnamurra Aquaponics: A Commercial Aquaponic Farm in Victoria, Australia", Aquaponics Journal, 1st Quarter 2006, Issue 40, pp. 22-25, 4 pages.
Carlos Leon Ramos, "Aquaponics Guadalajara", Aquaponics Journal, 1st Quarter 2006, Issue 40, pp. 12-13, 2 pages.
Geoff Wilson, "Canadian R&D Should Inspire Hydropanic Growers to Convert to Aquaponics", Aquaponics Journal, 1st Quarter 2006, Issue 40, pp. 26-28, 3 pages.
Geof Wilson, "UVI Presents Aquaponics at Soilles Conference in Singapore", Aquaponics Journal, 4th Quarter 2005, Issue 39, pp. 20-22, 3 pages.
Geoff Wilson, "Canadian R&D will be a Catalyst for Change as . . . Greenhouse Aquaponics Proves Superior to Inorganic Hydroponics", Aquaponics Journal, 4th Quarter 2005, Issue 39, pp. 14-17, 4 pages.
Dr. Nick Savidov, "Evaluation of Aquaponics Technology in Alberta, Canada", Aquaponics Journal, 2nd Quarter 2005, Issue 27, pp. 20-25, 6 pages.
Geoff Wilson, "Aussie University Adopts Aquaponics for Teaching", Aquaponics Journal, 4th Quarter 2004, Issue 35, pp. 14-15, 2 pages.
Wilson Andrew Lennard, "Aquaponics Research at RMIT University, Melbourne Australia", Aquaponics Journal, 4th Quarter 2004, Issue 35, pp. 18-24, 7 pages.
Rebecca L. Nelson, "Aquaponics Seminar, Queensland, Australia", Aquaponics Journal, 3rd Quarter 2004, Issue 34, pp. 8-9, 2 pages.
Carla MacQuarrie, "Future Aqua Farms, LLC Growing Strong in 2003", Aquaponics Journal, 1st Quarter 2003, vol. 2, No. 1, pp. 8-10, 3 pages.
Eric Hutchings, "Aquaponics Research on the Prairies, Brooks, Alberta, Canada", Aquaponics Journal, 4th Quarter 2003, vol. 7, No. 4, pp. 12-17, 6 pages.
Todd Harmon, "NFT Aquaponic Systems: A Closer Look, The Land, EPCOT, Walt Disney World, Orlando Florida" Aquaponics Journal, 4th Quarter 2003, vol. 7, No. 4, pp. 8-11, 4 pages.
James Rakocy, "UVI Aquaponic Technology Heads North to New Jersery", Aquaponics Journal, 1st Quarter 2003, vol. 7, No. 1, pp. 22-25, 4 pages.
Rebecca L. Nelson, "Kirby Peak Ranch, Ground Breaking Ceremony", Aquaponics Journal, 4th Quarter 2001, vol. 5, No. 4, pp. 12-14, 3 pages.
Rebecca Nelso, "The University of the Virgin Islands, Agriculural Experiment Station", Aquaponics Journal, Feb., Mar. 1999, vol. 5, No. 2, pp. 4-10, 7 pages.
Scott Jones, "The Aquaponics Team", Aquaponics Journal, Dec./Jan. 1997/1998, vol. 3, pp. 11-13, 3 pages.
James E. Rakocy et al., "Recirculating Aquaculture Tank Production Systems: Aquaponics—Integrating Fish and Plant Culture", SRAC Publication No. 454, Nov. 2006, pp. 16 pages.
Steve Diver, "Aquaponics—Integration of Hydroponics with Aquaculture", ATTRA, 2006, 28 pages.
Nick Savidov, Ph.D. et al., "Evaluation and Development of Aquaponics Production and Product Market Capabilities in Alberta" Ids Initiatives Fund Final Report, Aug. 17, 2004, 22 pages.
Office Action issued in the corresponding Chinese Application No. 200780033344.0 dated Mar. 16, 2011 (5 pages).
Office Action issued in corresponding Chinese Application No. 200780033344.0 dated Mar. 7, 2012 (10 pages).
Search Report issued in corresponding European Application No. 07784644.2 dated Jan. 5, 2012 (5 pages).

* cited by examiner

AQUAPONICS SYSTEM

FIELD OF THE INVENTION

The present invention relates to an aquaponics system. This invention has particular application to farming systems for combined breeding of fish and growth of vegetables, and for illustrative purposes the invention will be described hereinafter with reference to this application. However, it will be appreciated that this invention may find use in alternate applications, such as breeding crustaceans or other aquatic species and/or growth of any other suitable plant.

BACKGROUND OF THE INVENTION

Aquaponics involves the symbiotic integration of the growth of aquatic species with growth of plants. The general concept of the aquaponics system is that the waste products from the aquatic species are used as nutrients for the plant species. In utilising the nutrient-rich waste of the aquatic species, the plants somewhat cleanse the circulating water, making it suitable for the aquatic species to survive in.

Aquaponic systems are being increasingly recognised as having potential for solving some of the many problems facing modern agriculture and aquaculture systems. These problems include:
  A. Unsustainable and increasing water use in a world of diminishing water resources
  B. Land previously suitable for agriculture becoming prohibitively expensive or unavailable due to urbanisation and urban sprawl.
  C. As a consequence of point B above, the 'food miles' (distance from food production to end consumer) is rapidly increasing, resulting in a range of ecological and human health problems, such as breakdown of nutrient recycling, increased energy consumption and subsequent greenhouse gas emissions, loss of food freshness and nutritional quality, etc.
  D. Waste effluents and chemical pollutants from food production systems causing ecological and human health problems
  E. Loss of fertile soil.
  F. Net protein loss in conventional aquaculture and aquaponic systems in which ocean-caught protein sources are used as aquaculture feeds.

Although aquaponic systems have some potential for solving these problems, prior art aquaponic systems have had only limited success in realising this potential.

Accordingly it would be advantageous if an aquaponics system could be devised which may at least partially address the problems above or provide the public with a useful or commercial choice.

SUMMARY OF THE INVENTION

According to a first aspect of the present invention there is provided an aquaponics system including:
  a tank for housing at least one aquatic animal species;
  a plant growing apparatus for housing one or more plant species growing in an aqueous environment; and
  a biofilter module for receiving a waste stream comprising solid waste and water from the tank, the biofilter module comprising;
    a solids removal means; and
    a biological waste digestion unit for digesting solids from the solids removal means to produce plant nutrients, which biological waste digestion unit comprises a biological species that at least partially digests solid waste from said solids removal means to plant nutrients;
  whereby in use, said plant nutrients are transferred to the plant growing apparatus and at least a portion of the water is returned to the tank.

In a related aspect, the present invention provides an aquaponics system including:
  a tank for housing at least one aquatic animal species;
  a plant growing apparatus for housing one or more plant species growing in an aqueous environment; and
  a biofilter module for receiving a waste stream including waste and water from each of the tank and the plant growing apparatus, the biofilter module including:
    a large solids removal means; and
    a biological waste digestion unit for digesting solids to produce plant nutrients;
    wherein said biological waste digestion unit includes a biological species that at least partially digests waste from said aquatic species to plant nutrients;
  whereby in use, said plant nutrients are transferred to the plant growing apparatus and at least a portion of the water is returned to the tank.

Optionally the system may also include a nitrification means for treating water.

The nitrification means may include any nitrifying entity capable of nitrifying ammonia, for example it may include an appropriate chemical, a zeolite filter or any nitrifying microorganism. In a preferred embodiment the nitrification means may include one or more species of nitrifying bacteria, for example nitrosomas and nitrobacter. Preferably the nitrification means may also include a high surface area media, for example bio-balls. The nitrification means may include a tank for housing said nitrification entity, wherein said tank is separate from the plant growing apparatus.

According to a second aspect the present invention provides an aquaponic method for symbiotic rearing of one or more aquatic species and one or more plant species including;
  a) providing
    i) a tank which houses one or more aquatic animal species;
    ii) a plant growing apparatus which houses one or more plant species growing in an aqueous environment; and
    iii) a biofilter module for receiving a waste stream including solid waste and water from the tank, the biofilter module comprising a solids removal means and a biological waste digestion unit for digesting solids from the solids removal means to produce plant nutrients, which biological waste digestion unit comprises a biological species that at least partially digests solid waste from said solids removal means to plant nutrients;
  b) transferring solid waste from said tank to said biofilter module; and
  c) transferring said plant nutrients from said biofilter module to said plant growing apparatus.

In a related aspect, the present invention also provides an aquaponic method for symbiotic rearing of one or more aquatic species and one or more plant species. Preferably the method includes:
  a) providing
    i) a tank for housing at least one aquatic animal species;
    ii) a plant growing apparatus for housing one or more plant species growing in an aqueous environment; and iii) a biofilter module for receiving a waste stream including waste and water from each of the tank and the plant growing apparatus, the biofilter module including:
a large solids removal means; and
a biological waste digestion unit for digesting solids to produce plant nutrients;
wherein said biological waste digestion unit includes a biological species that at least partially digests waste from said aquatic species to plant nutrients;
b) housing said aquatic animal species in said tank and housing said plant species in said plant growing apparatus;
c) transferring water and waste from said tank to said biofilter module;
d) transferring plant nutrients and a portion of the water exiting said biofilter module to said plant growing apparatus; and
e) returning at least a portion of said water to the tank.

The design of these aspects of the invention may allow the provision of at least a partially closed circuit aquaponics system. In a preferred embodiment the invention provides a closed circuit system. A closed circuit aquaponics system is one in which the entirety of the wastes produced by the biological species in the system are recycled through the system with very little to no expulsion of waste (including aquatic species excrement and plant matter). A partially closed circuit aquaponics system is one in which expulsion of waste is minimal, with the majority of waste being recycled through the system.

The inventors have surprisingly and unexpectedly found that the use of a biological waste digestion unit independent of the plant growing apparatus allows both water and degraded waste to be recycled within the system without the need to continuously expel water and effluent from the system after it has passed through components of the system, whilst requiring reduced or even no plant media. This is obviously advantageous from a conservation perspective and may facilitate the potential use of aquaponics system in environments where they may not normally be suitable, for example in urban settings. Also the use of an aquaponic system in which minimal input of water is required, for example only such water that is required to replace evaporation from the system needs to be added to the system, is obviously advantageous in times of water shortage. Furthermore, the system may be more productive because higher levels of nutrients are retained within the system that can be used for increased plant growth. Regular input of food for the aquatic species may be required and similarly occasional cleaning (including expulsion) and replenishment of other inputs such as water may be required. Embodiments are envisaged where the primary food source for the aquatic species is also integrated into the system.

The tank containing the aquatic species may be any appropriate shape. In a preferred embodiment the tank may be designed to allow reversible unidirectional circular flow throughout the tank, for example the tank may include a baffle through the tank. Additionally the tank may include air or water jets to propel water in a particular direction.

The aquatic species may be any appropriate species, for example any species of fish, crustaceans, shellfish or molluscs. In a preferred embodiment the aquatic species is fish.

The solids removal means may be any appropriate means for separating particulate matter from water or particles of a predetermined minimum size (typically large particles such as particles of 50 microns or more) from smaller particles and water (the latter being termed a large solids removal means).

In a preferred embodiment the solids removal means includes a filter, such as a drum filter. The filter may be appropriately sized depending on the aquatic species housed in said tank. In a preferred embodiment the filter allows delivery of the solids stream to the biological waste digestion unit with minimal water content.

In another embodiment, the solids removal means includes a swirl separator, which is a conical chamber which passively settles the heavier solids in the waste stream. The overflow to the swirl separator may, for example, be directed to another solids removal means, such as a filter as described above, for the removal of solid matter that has not been captured by the swirl separator.

It is also possible for the solids removal means to include more than one system for separation/removal of solids (or alternatively expressed, the system may comprise more than one solids removal means). For example, the solid removal means can include both a swirl separator and a filter, such as a drum filter. In a particular embodiment, the different systems are supplied in parallel from the tank e.g. a swirl separator is supplied with a waste stream from the bottom, or a lower portion, or the tank, typically gravity fed. A filter is supplied with a waste stream from a stand pipe, or similar, at the surface of the water in the tank.

The system may also comprise a foam fractionator or 'protein skimmer' connected to the output of a nitrification means (described in more detail below). Water on leaving the nitrification means may be passed through such a foam fractionator or 'protein skimmer' whereby fine suspended particles and dissolved proteins are removed from the water as surface foam. This waste stream in the form of a foam is then delivered to the biological waste digestion unit.

The solid waste, such as a rich sludge, collected by the one or more components of the solid removal means is transferred to a biological waste digestion unit. In the case of filters, such as drum filters, the collected solid waste is typically periodically back-washed by water in the system, for example using water delivered onto the filter mesh or screen by pressurised jets. In the case of a swirl separator, the solid waste can be transferred by opening a valve at the base of the separator to drain the separator, allowing solids to drop into the biological waste digestion unit by gravity and/or with the assistance of some system water.

Other suitable solids removal means and methods for transferring collected solids to the biological waste digestion unit will be readily apparent to a person skilled in the art.

In a preferred embodiment the biological species in the biological waste digestion unit is a species of worm. In a preferred embodiment the biological waste digestion unit is a worm unit. Other suitable biological species include insect larvae, as are described in more detail below.

The role of the biological species in the biological waste digestion unit, such as compost worms, in simplistic terms, is to convert solid wastes from the fish tank into a form more suitable (e.g. worm castings) for reintroduction into the system. Uneaten fish feed and faeces, if not thoroughly processed, is a potential source of disease. Once passed through the worm's gut however the castings can safely be reintroduced as a liquid plant food that also supports a colony of micro-organisms carrying out other important functions such as buffering, nutrient cycling and disease repression.

The plant growing apparatus may be any suitable apparatus that allows the growth of plants in an aquatic environment. For example the apparatus may contain hollow tubes through which water and nutrients exiting the biofilter module may be passed, with upper opening for entry of plant roots. The plant growing apparatus may be a stacked apparatus including multiple layers of plant troughs. For example, the apparatus may take the form of a multiple level A frame or ladder type structure.

Since water exiting the plant growing apparatus will generally include some solid matter including plant debris and growth media (if used), this water is typically passed through, or transferred to, a filter to separate the solid matter from the water prior to the water being directed to the tank. In a preferred embodiment water exiting the plant growing apparatus is directed back to the solid removal means, such as to a filter/drum filter component of the solid removal means. The apparatus may optionally include an insect larvae production module. Said module would include a reversibly sealable container for housing organic waste and a suitable insect species, an insect larvae outlet pipe to direct larvae from said container and optionally an insect larvae collection means.

The size of the components of the current system will be generally co-dependent, i.e. the size of the tank will affect the number of aquatic organisms which. may be maintained, which will in turn effect the amount of nutrients produced via the biological waste digestion unit, which in turn will effect the amount of plants that may be grown. In a preferred embodiment the plant growing apparatus may be able to grow sufficient plants per square meter to take up the available nutrients from the aquatic species maintained in the tank in the same surface area as the tank and biological waste digestion unit combined. For example, a 10,000 liter tank and its associated biological waste digestion unit may require a surface area of approximately 12 sqm. An appropriate aquatic species in a tank this size in optimal conditions will generally produce enough nutrients to allow growth of approximately 2,500 appropriate plants, e.g. lettuce plant. Therefore preferably the plant growing apparatus in this scenario would provide 2,500 plant spaces in a surface area of 12 sqm, such that the two functions (fish production and plant production) could be superimposed on the same footprint and so significantly increase the system's production per square meter.

In one embodiment the current system is designed to be used in urban farming environments where space is premium. To facilitate such an embodiment the current system has the benefit of being able to be scaled appropriately depending on the requirements. For example in an urban setting the components of the system would be stacked where appropriate, e.g. the plant growing apparatus may be a suitable vertical growing apparatus, and the biological waste digestion unit may be vertically orientated. Additionally, the individual components of the system may be stacked vertically in an appropriate order, for example, plant growing apparatus above biological waste digestion unit, above tank. Other functions not requiring sunlight may also be vertically stacked below the system, for example, the insect larvae production module, production of mushrooms or compost production may also be stacked beneath the vegetable production system.

In embodiments where the system may be vertically stacked the system has potential use in a number of settings in which it would not previously been suitable for an aquaponics system to be established. For example, the stacking may allow the use of the system in urban settings and densely populated areas where horizontal space is restricted. Additionally the partially closed nature of the system, as described above, may also facilitate its use in such settings as there is no issue with disposal of waste or water.

Some closed or partially closed circuit aquaponics systems do exist, however such systems house any waste converting components within the media held in the plant beds. These beds contain worms and other waste-converting organisms, which turn solid waste into 'plant food' which is then taken up by plants growing in the gravel beds. In such systems all water and solid wastes are passed through the plant media beds.

Such systems have limitations which the current invention aims to address. Cleaning and maintenance of the system is difficult as the plant media need to be removed from and replaced into the plant beds regularly as waste builds up. This is quite tedious and labour intensive. Furthermore, the raw waste from the tank is held in the media through which the full flow of water continually passes. The system of the current invention is designed such that the solid wastes are quickly isolated such that only a small percentage of water passes through untreated waste. The current system is thus able to maintain a much higher fish stocking density without fear of biological problems or collapse. Consequently, the higher fish density results in more concentrated nutrients within the system and increased potential for plant growth. Additionally, the use of plant media such as gravel in the plant beds adds a great deal of weight to the system making it difficult to modify if already established and also renders it unsuitable for vertical stacking.

In the specification and claims the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

BRIEF SUMMARY OF THE FIGURES

The present invention will now be described by way of the following description having reference to the figures, wherein.

Figure 1:
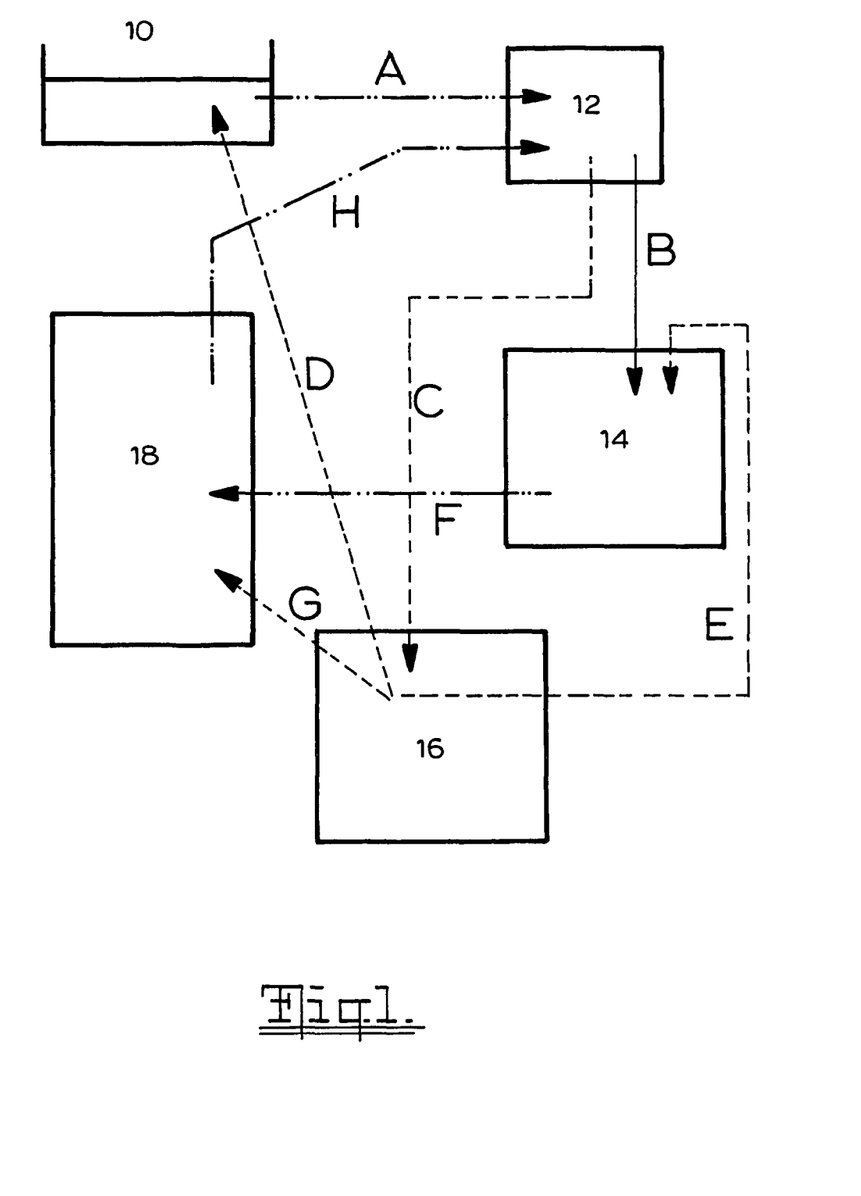
FIG. 1 depicts one embodiment of an aquaponics system in accordance with the current invention.

In FIG. 1 an aquaponics system in accordance with the present invention is depicted. The tank (10) is designed to house and maintain any suitable aquatic class/es including (but not limited to) fish and/or crustaceans. Water and waste (including food debris and effluent) is regularly removed from the tank (10) actively (eg by pumps) or passively (eg by gravity), or a combination of both, and delivered to a large solids removal means (12) (Arrow A). The dot-dash lines in FIG. 1 denote the movement of both water and solids.

Upon entering the large solids removal means (12) the large particles are separated from the water and smaller particles (including dissolved and undissolved particles). At this point there are two distinct streams, the dissolved stream including the water and smaller particles that pass through the filter and the solids stream, including the solid particles retained by the filter. The dissolved stream is represented in FIG. 1 by the dashed arrows. The solids stream is represented by the solid arrows.

The solids stream is directed (Arrow B) to the biological waste digestion unit (14), where the solids including food debris and effluent are digested. The dissolved stream exiting the large solids removal means (12) may be transferred directly to the plant growing apparatus (18), back to the tank (10), or in a preferred embodiment is transferred (Arrow C) to a nitrification means (16).

From the nitrification means a portion of the water is directed (Arrow D) back to the tank (10), while the remainder is directed (Arrow E) to the biological waste digestion unit (14) to ensure there is adequate liquid to allow nutrients released by digestion of the solids stream by the biological species within the biological waste digestion unit (14) to be flushed through the unit (14).

Nutrients released from the solids stream carried in water flushed through the biological waste digestion unit (14) are transferred (Arrow F) to the plant growing apparatus (18). If required additional water may be directed (Arrow G) from the nitrification means (16) to aid in flow of nutrients to and through the plant growing apparatus (18). This additional water may be added to the nutrients and water exiting the biological waste digestion unit before it enters the plant growing apparatus (18). Water exiting the plant growing apparatus (18) will generally include some solid matter including plant debris and growth media (if used) and is thus passed through, or transferred to, a filter to separate the solid matter from the water prior to the water being directed to the tank (10). In a preferred embodiment water exiting the plant growing apparatus (18) is directed (Arrow H) back to the large solid removal means (12) where it re-enters the loop described above.

In embodiments where the nitrification means (16) is not present, water exiting the plant growing apparatus (18) is directed back to the tank (10), preferably passing through a filter to separate any solids including growth media and plant debris from the water and dissolved particles before the water is directed to the tank.

Water and waste from the tank (10) first enters the large solids removal means (12). The large solids removal means may be a filter. Any suitable filter may be used including a drum filter (e.g. of the type supplied by Hydrotech, Sweden), or any other type of solids removal filter. Solids particles larger than a specified size (dependent on the filter) are collected within the filter. Preferably the filter will be designed to collect solid particles larger than around 30 microns, such as larger than about 40 or 50 microns. The remaining water and smaller particles will pass through the filter.

Optionally the water and waste from the tank may pass through more than one large solids removal means. For example the water and waste may pass through a series of filters with decreasing filter sizes. Alternatively the water and waste may pass through a separator, e.g. a swirl separator, before passing through another large solids separation means, such as the filters described above. In a particular embodiment, the different solids removal means are supplied in parallel from the tank e.g. a swirl separator is supplied with a waste stream from the bottom, or a lower portion, or the tank, typically gravity fed. A filter is supplied with a waste stream from a stand pipe, or similar, at the surface of the water in the tank.

As outlined above, after passing through the large solids removal means (12), there are two distinct streams, the dissolved stream including the water and smaller particles that pass through the filter and the solids stream, including the solid particles retained by the filter.

The dissolved stream will generally include relatively high levels of ammonia. Ammonia is quite toxic to many aquatic species. Thus the current system optionally includes a nitrification means (16) which facilitates the conversion of ammonia to nitrite and subsequently nitrate, both of which are less toxic. The nitrification means (16) may include any suitable means of nitrifying ammonia. In a particular embodiment the nitrification means (16) includes a chamber which provides a suitable habitat for nitrifying bacteria. For example the chamber may include high surface area media (for example bioballs or any other suitable media) to allow a large number of bacteria to colonise the filter. Any nitrifying bacteria may be used, for example nitrosomas and nitrobacter. Alternatively the water may be passed through a zeolite filter.

As different species of plants prefer different ratios of nitrate and ammonia, dependent upon the plant species being cultivated, fluid can be drawn off from various points in the system to optimise plant growth. For example, for plants preferring a higher percentage of ammonia, fluid can be drawn off from the dissolved loop after water has passed through the large solids removal means but before it has entered the nitrification chamber. In such embodiments, to decrease the level of ammonia in the water being returned to the tank (10), the water exiting the plant growing apparatus (18) may pass through a nitrification means prior to being returned to the tank (10). Alternatively for plants preferring less ammonia and more nitrate, fluid can be drawn off after the nitrification chamber. Optionally, fluid drawn off from either of these points can then be combined with nutrient-rich fluid accumulating in the biological waste digestion unit (14) before being delivered to the plant growing apparatus.

In a preferred embodiment fluid passes through the nitrification means (16) prior to entering the biological waste digestion unit (14). The nitrification means (16) receives and processes the dissolved stream prior to the dissolved stream being directed to the biological waste digestion unit (14). Advantages of such an arrangement are that the ammonia levels passed to both the biological waste digestion unit (14) and the plant growing apparatus (18) is reduced, and furthermore, direct contact between waste (fish faeces and uneaten food) and plants is greatly reduced as there is a biological buffer or converter between each part of the system i.e. solids pass through the biological waste digestion unit (14) for processing and dissolved ammonia passes through the nitrification means (16) before reaching the plants. This clearly has biological and management advantages and may aid in meeting organic certification standards unlike many of the existing aquaponic systems.

As the dissolved stream passes through the nitrification means (18) at least a portion of the ammonia is converted to nitrite, at least a portion of which is converted to nitrate. A portion of the dissolved stream is then directed back to the tank (10) (Arrow D) through an inlet, a portion is directed to the biological waste digestion unit (14) (Arrow E) to allow the provision of sufficient water through this unit and on to the plants. Optionally a portion of the dissolved stream may be directed from the nitrification means (16) to the plant apparatus (18) (Arrow G) if the dissolved stream exiting the biological waste digestion unit (14) is particularly concentrated). This portion of the dissolved stream may combine with that exiting the biological waste digestion unit prior to entering the plant apparatus, or it may be directed straight to the plant growing apparatus (18). The water may be directed passively (eg by gravity) or actively (eg by the use of a pump) or a combination of both. In a preferred embodiment the overall ammonia level of the system is maintained below 2 parts per million.

Optionally, from either the large solids removal means (12) or the nitrification means (16) the dissolved stream may be directed to a small particle separator to allow the removal of dissolved proteins and/or solid particles which may have passed through the large solids removal means (12). Any appropriate small particle separator may be utilised, for example a foam fractionator which separates the small particles from the water by passing air through a column of water such that the small particles separate as foam which is collected at the top of the column. The foam may be directed to the biological waste digestion unit (14) for subsequent conversion, while the water may be directed back to the tank (10).

If allowed to build up, the high organic load contained in the solids loop has a profound affect on water quality and system health. If left untreated there is a real risk of collapse of the entire system and fish death. Thus, the solids stream including the solids retained by the large solids removal means (12) is transferred from the large solids removal means (12) to the biological waste digestion unit (14). This transfer may be facilitated by a flushing means, for example spray jets, which periodically back flush the large solids removal means (12) with water from either the tank (10), nitrification means (16) or plant growing apparatus (18) or from an external water source.

The biological waste digestion unit (14) includes biological species that are able to digest the waste from the aquatic species that flows through to the unit to produce a nutrient source. The presence of the biological waste digestion unit (14) allows recycling of a large proportion of the waste generated by the aquatic species such that it is usable as nutrients for the plants. This means that the amount of discharge from the system may be significantly reduced, or completely eliminated, compared to traditional systems.

Figure 2:
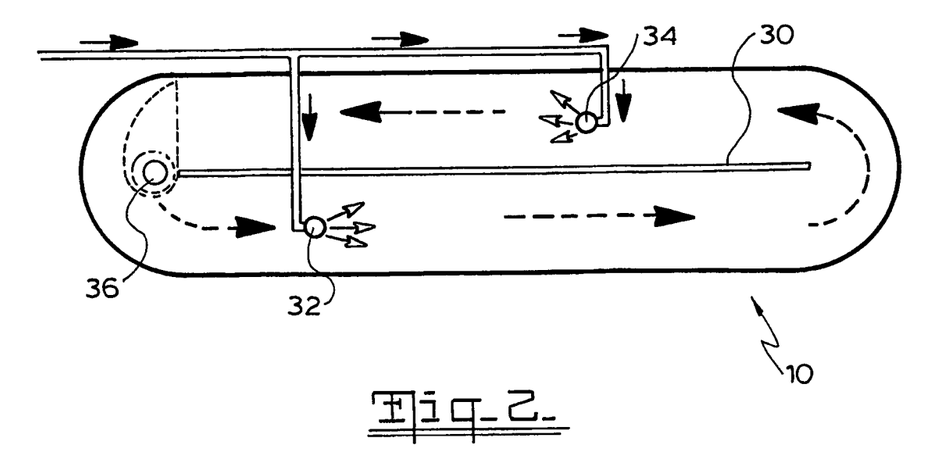
FIGS. 2 to 4 depict a tank and associated components suitable for use in an aquaponics system in accordance with the current invention.

FIG. 2 depicts a suitable tank (10) for use in the current system. While the tank (10) may be of any shape or size required depending on the use of the system and/or the dimensions of the area in which it is to be housed, in a preferred embodiment the tank (10) may be rectangular with rounded ends. The tank (10) may optionally include a baffle (30) running lengthways through the middle of the tank (10), stopping short of the ends. Such an arrangement may facilitate better water flow throughout the tank (10). One or more inlets (32, 34) returning treated water and/or introducing new water to the tank (10) may be specifically directed to ensure that the water circulates adequately in a particular direction. The direction of such inlets (32, 34) may be changeable.

Any suitable aquatic class may be housed in the tank (10), for example fish or crustaceans. One or more separate aquatic class or species may be housed in the tank (10) at any one time, for example crustaceans and fish, or more than one distinct fish species may be housed together.

In one embodiment there may be a series of linked tanks in series, for example fish in the first tank, with the water then flowing to a second tank in which the fish waste is partially utilised by crustaceans, and then subsequently flowing to the biofilter for further conversion.

In preferred embodiments the aquatic species may be able to tolerate fresh water or brackish water, although it is envisioned that the system may be adapted to facilitate the use of aquatic species that require higher salt concentration, e.g. concentrations similar to sea water. An exemplar aquatic species is barramundi.

Water from the tank (10) is transferred to the biofilter module including a large solids removal means (12) and a biological waste digestion unit (14). This transfer may occur passively, for example due to gravity, or actively, for example the water may be pumped from the tank. As exemplified in FIGS. 2, 3 and 4 in a preferred embodiment the tank (10) includes a lower drain (36) which captures and allows transfer of water and solid wastes which have dropped to the bottom of the tank (10) and a surface drain (38) which captures and allows transfer of water and any floating wastes.

Figure 3:
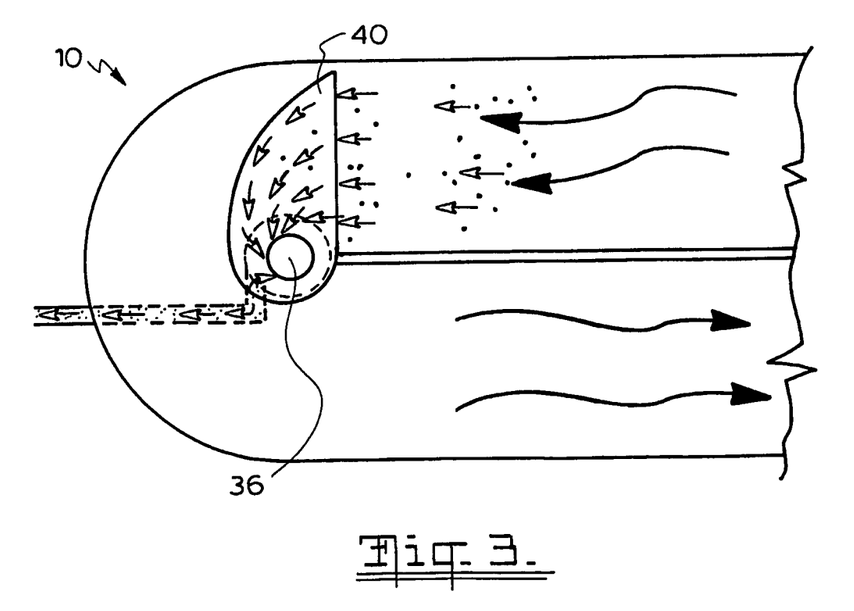
Figure 4:
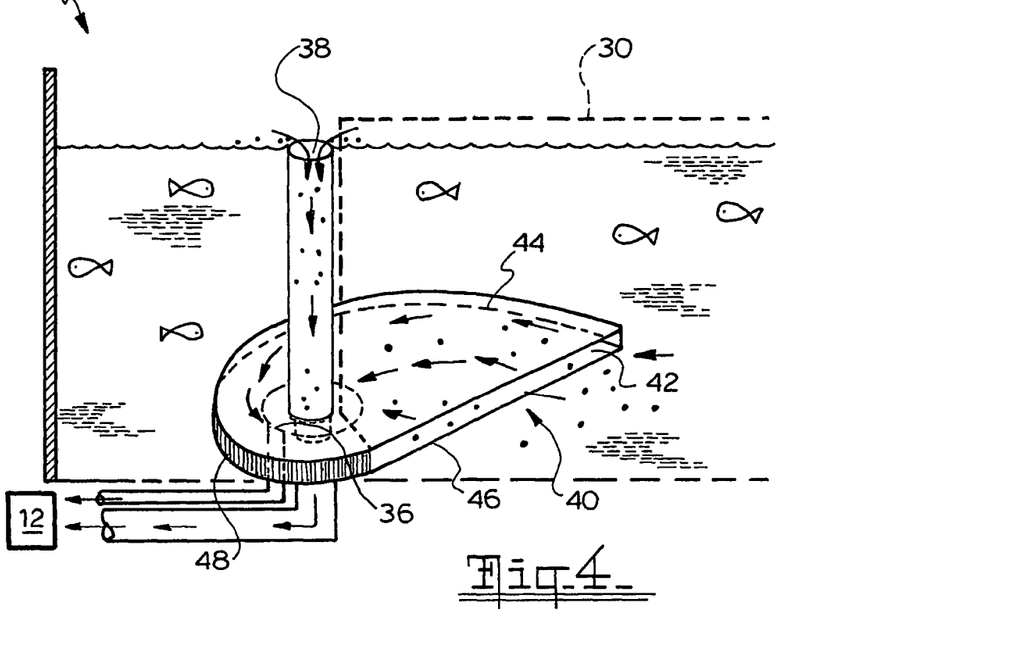

In one embodiment a waste guidance means (40) may be used to guide wastes to the lower drain (36). The waste guidance means (40) is designed such that a vacuum is created at the open face (42), drawings solids towards the lower drain (36). The waste guidance means (40) may be of any appropriate shape. It may span from the lower drain (36) at least partially to at least one wall of the tank (10). The waste guidance means (40) includes an open face (42), preferably opened towards the direction of oncoming water flow. Upon entering the waste guidance means (40), waste is directed to the lower drain (36).

While the waste guidance means may be separate unit positioned on or above the floor of the tank, it may also be designed to include the floor of the tank. The embodiment depicted in FIG. 4, includes a nautilus shaped plate (44), positioned just above the floor of the tank (10) and affixed to the surface drain (38). The open face (42) is bounded by the floor (46) of the tank (10) at its lower edge and the plate (44) at its upper edge. A water impermeable seal (48) seals the remainder of the waste guidance means (40) to the floor of the tank (10). A vacuum is created drawings solids and water underneath the plate (44) and into the lower drain (36).

The biological waste digestion unit may contain one or more components housing said biological species. The biological waste digestion unit may include more than one component housing said biological species, wherein at any one time one or more of the components may be receiving the solids stream while one or more other components are not. For example the components may be moved between one or more receiving positions and one or more non-receiving positions, wherein when in a receiving position a component receives said solids stream. In a preferred embodiment the component may include one receiving position and more than one non-receiving position. The unit may include a rotation apparatus to allow rotation of one or more components between receiving and non-receiving positions. Alternatively flow of the solids stream to each component may be controlled by a flow control means, for example valves, flow gates etc.

Figure 5:
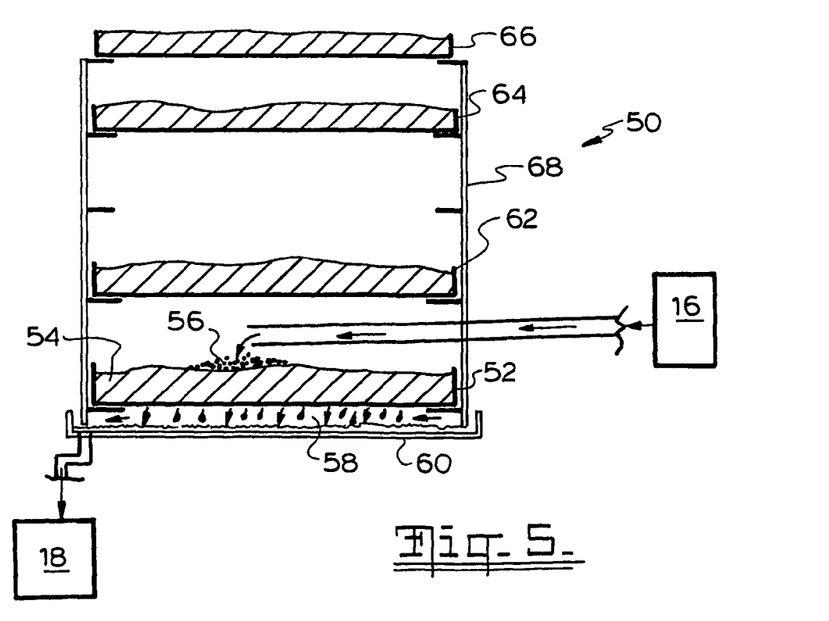
FIG. 5 depicts a biological waste digestion unit suitable for use in an aquaponics system in accordance with the current invention.

In a preferred embodiment as depicted in FIG. 5, the biological waste digestion unit (14) may be a worm unit (50). The worm unit (50) may include at least one tray (52) which holds compost material and worms (54). Any appropriate worm species may be utilised, including "compost worms". Worms provide an environmentally sound alternative to chemical methods of waste conversion. By passing the waste through the worms' guts, disease agents such as heterotrophic organisms are killed and the by-product, worm castings, provides a mineralised plant food. Furthermore, the act of processing waste via compost worms also produces chelating agents such as fulvic and humic acids which further assist in nutrient uptake by plants. Optionally, the worm trays may be inoculated with strains of bacteria and fungi that further assist the process of mineralization, and increase the systems ability to buffer the pH and cycle nutrients, therefore potentially adding to the overall stability and efficiency of the system.

The solids stream (and foam from the foam fractionator if present) (56) is directed to the worm unit (50), optionally along with a small amount of backflushed water from the large solids removal means and/or the routed water from the nitrification means (16). Preferably liquid entering the worm unit is kept to a minimum or is absent. Water and worm leachate (58) that passes through the compost (56) will be relatively nutrient rich and is collected underneath the worm trays in a collection tray (60). It is then directed to the plant growing apparatus (18). The water may be directed passively (eg by gravity) or actively (eg by the use of a pump) or a combination of both.

In preferred embodiments the worm unit may contain a number of worm trays (52, 62, 64, 66) which are able to be rotated such that any or all of them may be actively receiving input from the solids stream and optionally the nitrification chamber at any one time. Alternatively each tray (52, 62, 64, 66) may be opened and closed with a control means, for example a valve or flow gate, such that the solids stream can be delivered to the various tray receiving positions in a sequence and timing that optimises the functioning of the worm unit.

In the embodiment depicted in FIG. 5 the unit has a five tier stacking apparatus (68) where each tier is equipped to house a single worm tray (52, 62, 64, 66). More or less tiers and thus worm trays would also be appropriate for the current system.

Optionally the unit (50) may have one or more worm trays (52, 62, 64, 66) in a receiving position at one time and the remaining trays in a "rest" position trays in a receiving position (52) would be actively receiving the solids stream and/or water exiting the nitrification means. Trays in the "rest" position (62, 64, 66) would not be actively receiving input from the solids stream or the nitrification chamber, however worms would be processing the biological waste previously delivered to the tray via the solids stream. The trays may be rotated at specific intervals dependent upon the size of the trays and the volume and concentration of the solids stream. The subsequent worm castings are relatively non-toxic and provide nutrients for the plant system. By regularly rotating the trays (52, 62, 64, 66) within the unit (50), minimal fresh waste is exposed to the continual water flow within the system, hence achieving a more stable and healthy system.

By keeping most of the fresh waste isolated from the water flow until it is processed via the worms, inoculation pressure of harmful organisms is kept to a minimum within the system. The 'ecosystem services' required of the biofilter in this system are therefore less than systems in which most of the waste remains within the water flow, allowing a more compact unit. The system is configured to maximise recycling of nutrients while minimising disease potential.

Figure 6:
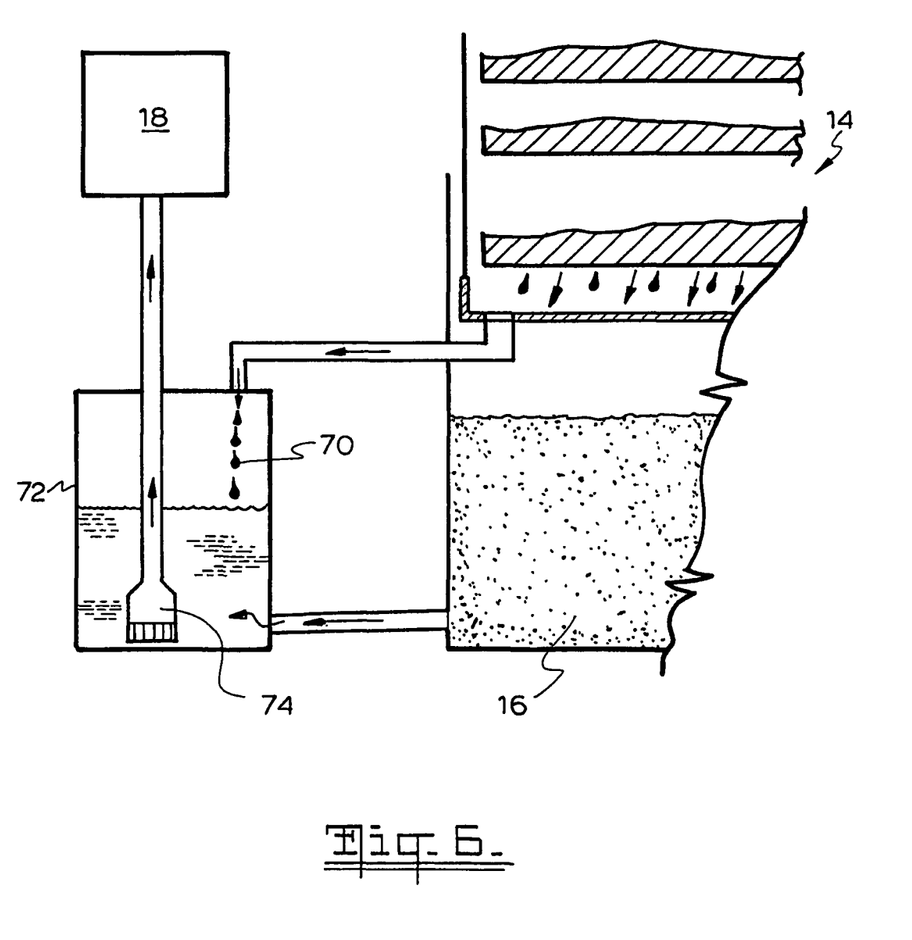
FIG. 6 depicts a suitable transfer of streams to the plant growing apparatus in accordance with the current invention.

As outlined above and as depicted in FIG. 6, nutrient rich water exiting the biological waste digestion unit (14), and optionally a portion of the dissolved stream directed from the nitrification means (16), is directed to the plant growing apparatus (18). The water may be directed passively (eg by gravity) or actively (eg by the use of a pump) or a combination of both. In FIG. 6, nutrient rich water (70) exiting the biological waste digestion unit (14) and a portion of the dissolved stream directed from the nitrification means (16) is directed to the plant growing apparatus (18). In this embodiment nutrient rich water (and leachate) (70) from the worm unit and water directed from the nitrification means (16) is combined in an intermediate container (72) and actively transferred by a pump (74) to the plant growing apparatus (18).

In another alternative, water may be directed from the nitrification means (16) to the leachate exiting the biological waste digestion unit (14). For example, where a worm unit is present as described in FIG. 5, water from the nitrification means (16) may be directed to the collection tray (60), prior to the lechate and now added water being directed to the plant growing apparatus (18).

The plant growing apparatus (18) may be any appropriate apparatus. In a preferred embodiment the system includes growing troughs in which the plants roots are positioned. The nutrient rich water exiting the biological waste digestion unit is received in the growing troughs in which the plants' roots are immersed. The plants extract the nutrients from the nutrient rich water facilitating plant growth.

The water exiting the plant growing apparatus (18) is relatively nutrient reduced and is subsequently returned to the large solids removal means (12). The nutrient reduced water may be returned to the large solids removal means (12) passively (eg by gravity) or actively (eg by the use of a pump) or a combination of both. This ensures that any solids present in the nutrient reduced water, e.g. potting mix, plant debris etc are captured by the large solids removal means and become part of the solids stream which is subsequently directed to the biological waste digestion unit. Thus, solids over the selected filter size are not sent to the tank or nitrification means.

Preferably the plant growing apparatus (18) will be designed to maximise production per square meter of land required. Preferably a vertically stacked plant growing apparatus would be used. Any form of vertically stacked plant growing apparatus may be utilised, for example rotating NFT systems, Ferris wheel type arrangements, A frame arrangements.

Figure 7:
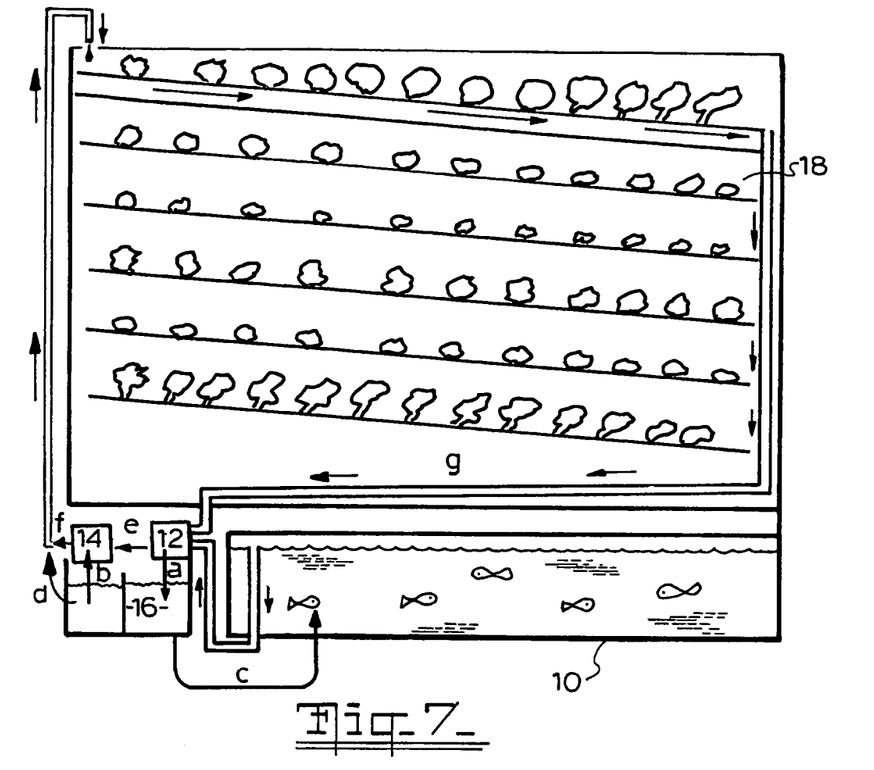
FIG. 7 depicts the interaction of preferred system components in accordance with the current invention.

As seen in FIG. 7, water and solids from the tank (10) is directed to the large solids removal means (12). The dissolved stream is directed to the nitrification means (16) (Arrow a), and divided to the biological waste digestion unit (14) (Arrow b), back to the tank (10) (Arrow c), or to join the nutrient rich water exiting the biological waste digestion unit (14) (Arrow d). Water from the nitrification means (16) may also be directed directly to the plant growing apparatus (18). Solid matter filtered by the large solids removal means (72) is directed to the biological waste digestion unit (14) (Arrow e). Nutrient rich water exiting the biological waste digestion unit (14) and any water directly applied from the nitrification means (16) is directed to the plant growing apparatus (18) (Arrows f and d respectively). Remaining water and solid matter (including plant debris and growth media) exiting the plant growing apparatus (18) is directed back to the large solids removal means (12) (Arrow g) to be reprocessed through the system.

Any suitable plant may be grown in the system. The system may support more than one plant species. Exemplar species include lettuce, asian greens, tomatoes and other fruiting vegetables, strawberries, leafy greens, wheat grass, wasabi, sprouts, herbs, and water cress.

The plant growing apparatus may contain soil, a suitable soil substitute (for example potting mix or gravel), or no permanent growth medium at all. In preferred embodiments the plant growing apparatus contains very little or no permanent growth medium. The advantages of including low levels of growth medium include the reduction of solid debris being filtered by the system such that the filters will require maintenance and replacement less often, and the overall weight of the plant growing apparatus is reduced. The latter advantage is particularly important with respect to embodiments of the invention that are vertically stacked to reduce the horizontal footprint of the system.

Figure 8:
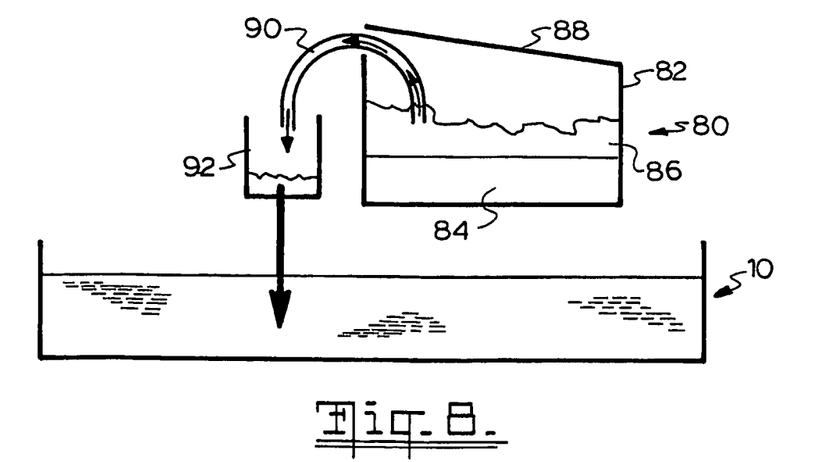
FIG. 8 depicts an insect larvae production module suitable for use in an aquaponics system in accordance with the current invention.

In one embodiment, the primary nutrients fed to the aquatic species is insect larvae (either fresh or dehydrated). In such an embodiment the apparatus in accordance with the invention may additionally include an insect larvae production module. An exemplary insect larvae production module is depicted in FIG. 8.

The insect larvae production module (80) includes a container (82) for housing organic waste (84) and insect larvae (86). The container (84) also includes a lid (88) to allow manual access while generally inhibiting the larvae from leaving the container (82). The module (80) may additionally include a larvae outlet pipe (90). Where a larvae outlet pipe (90) is present, the lid (88) is arranged such that the larvae are unable to leave the container (82) by any means other than the larvae outlet pipe (90). The larvae outlet pipe (90) may be associated with any suitable larvae collection means (92), from which the larvae can be transferred to the tank (10) as a nutrient source for the aquatic species. Transfer from the larvae collection means (92) to the tank may be manual (e.g. may require a user to transfer larvae) or automatic (e.g. the larvae collection means may include means for mechanically transferring larvae to the tank (10) such as by a series of active pumping pipes or the larvae collection means may be positioned above the tanks and include a timer release which allows release of a certain amount of larvae at pre-determined times). Alternatively, the larvae outlet pipe (90) may be directed directly to the tank/s (10), either on a preset time release or continual basis.

The "organic waste" fed to the insect larvae may be any suitable organic waste including human food scraps. Alternatively/additionally, the larvae may be fed on excess waste collected in the system's waste digestion unit. As the larvae move through their life cycle they will begin to pupate, at which time they will naturally begin to leave the insect larvae production module. The larvae outlet pipe (90) promotes movement to the collection means (92).

In a preferred embodiment the preferred species would be the larvae of the Black Soldier Fly (*Hermetia illucens*), however any suitable insect species could be used. Preferred appropriate species should be active consumers of organic waste (for example food scraps), have a relatively short life cycle (eg be ready to pupate within a few weeks), should, upon reaching the mature stage, automatically evacuate their stomach contents (providing a cleaner source of fish feed), and should be self-harvesting (i.e. have a natural tendency to leave the waste site and crawl to a suitable site for pupation. At this time the larvae will crawl up a ramp and along a larvae outlet pipe (90) and drop into a larvae collection means (92) ready for direct use as fish feed). While species possessing all of these characteristics are preferred, species that do not have all of these characteristics may be used in the system. For example, if a species is not self-harvesting a user may harvest the larvae manually and transfer to the tank/s.

In one embodiment, if fish fingerlings or small fish species are used the larvae may need to be processed into a smaller-sized feed. When using such species or fingerlings, the larvae can be dried and processed into a small pellet until the fish were large enough to handle full-sized live larvae. Alternatively the larvae may be crushed or processed in any other way which lessens the size thereof.

One preferred species of insect is the Black Soldier Fly (*Hennetia illucens*). With this species the digestion of waste to larvae is very quick, a high percentage of nutrients are captured by the larvae and consequently fed to the fish (and consequently the aquaponic plants). A high percentage of nitrogen is maintained in the digestion that would be lost, for example, through aerobic composting. The nutritional value of the Black Soldier Fly larvae is high and very suitable as a feed source for fish, consisting of:

42% protein
  35% fat
  a suitable amino acid profile
  dry weight 44% of the wet weight, which is much higher than compost worms or house fly larvae.

Another benefit of the Black Soldier Fly larvae is that it out-competes housefly larvae, so potential fly problems are eliminated. Although the larvae would be harvested before pupation, it would not be a problem if accidental pupation occurred, as the adult black soldier fly is not a human pest species and does not enter houses or buildings.

Most aquaculture and aquaponic systems rely on commercially produced fishmeal pellets as their feed source. Fish are harvested from the sea, processed into dry pellets and then fed to fish on aquaculture or aquaponic farms. Unfortunately, less fish are harvested than was originally extracted from the ocean to produce the feed pellets i.e. a net loss of protein which is ecologically inefficient as well as expensive in economic terms. As the current system has the option to operate on urban (or rural) waste as the main nutrient input (via the larvae production module), it is potentially significantly more ecologically efficient, as well as being potentially more profitable.

The present invention has addressed these limitations by providing the waste treatment components of the system independent of the plant growing areas. This has allowed the use of very little or no plant media at all within the plant beds. Surprisingly, this has allowed the applicant to provide a system which may provide higher production per square metre than existing traditional aquaponics systems in the virtually complete absence of waste effluents.

While each of the advantages offered by the present invention on their own provide significant advances over the traditional methods and systems, when considered together the advantages are even greater. The vertical stacking, and subsequent reduced footprint, may be an advantage in any situation where land for food production is expensive or there are other reasons for minimising the footprint. For example, the greenhouse growing regions in southern Spain have been criticised as even though they are on rural land, the large greenhouses are becoming so prevalent they are becoming an aesthetic problem. Furthermore, the current invention may also aid in the reduction of problems associated with the high level of effluents in such a region due to its at least partially closed nature.

Similarly on land that has not only high monetary value, but cultural, recreational, biological value etc the current system is useful. For example in environmentally sensitive areas, or island communities etc it is advantageous to produce the local food needs in the minimum possible land area.

Another advantage of vertical stacking and subsequent reduced footprint is that greenhouse infrastructure and running costs, as well as land acquisition costs can be minimised. Additionally, the use of more compact greenhouses allows for a more cost effective application of Integrated Pest Management (IPM) systems. For example, the use of total exclusion netting and other 'soft' (non-toxic) methods of pest control and management may be viable with the current invention that may be not cost effective for less intensive greenhouse systems.

It is also important to produce food close to where it is consumed to reduce costs and 'greenhouse gas' emissions due to consumption of fossil fuels used in transport. As most of the world's population live in and around urban areas it is essential for food production systems to be viable on land close to where the majority of people live. The current invention has the benefit of combining vertical stacking, minimal or no effluents, and optionally the ability to use non-toxic pest management, allowing the system to be cost-effective, socially acceptable, and ecologically sustainable in urban and other niches not previously suitable for agricultural production.

The world trend is that there is less and less land available for agriculture which needs to feed more and more people, while still maintaining all the biological and other services that land and natural ecosystems provide. It is therefore imperative to produce food in the minimum possible space and with the minimum possible ecological impact.

Unless defined otherwise, all technical and scientific terms used herein have the same meaning as commonly understood by one of ordinary skill in the art The various features and embodiments of the present invention, referred to in individual sections above apply, as appropriate, to other sections, *mutatis mutandis*. Consequently features specified in one section may be combined with features specified in other sections, as appropriate.

Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. An aquaponic method for symbiotic rearing of one or more aquatic species and one or more plant species comprising:
    a) providing
        i) a tank which houses one or more aquatic animal species;
        ii) a plant growing apparatus which houses one or more plant species growing in an aqueous environment; and
        iii) a biofilter module for receiving a waste stream including solid waste and water from the tank, the biofilter module comprising a solids removal means and a biological waste digestion unit for digesting solids from the solids removal means to produce plant nutrients, wherein the biological waste digestion unit comprises a biological species that at least partially digests solid waste from said solids removal means to plant nutrients, and further wherein the biological digestion unit comprises a plurality of trays which are able to be rotated such that the trays are actively receiving solids from the solids removal means when in a receiving position and not receiving solids from the solids removal means in a non-receiving position, and wherein only a subset of the total number of trays are in the receiving position at any time;
    b) rotating the subset of the total number of trays in the receiving position to the non-receiving position such that the subset of the total number of trays in the non-receiving position do not receive input of solids from the solids removal means, whilst the total number of trays process the solid waste from said tank;
    c) transferring solid waste from said tank to said biofilter module; and
    d) transferring said plant nutrients from said biofilter module to said plant growing apparatus.

2. A method according to claim 1 wherein the biofilter module receives a waste stream including waste and water from the plant growing apparatus.

3. The method of claim 1, wherein the subset of the total number of trays in the receiving position also receives water from a nitrification means.

4. An aquaponic method for symbiotic rearing of one or more aquatic species and one or more plant species comprising;
    a) providing
        i) a tank which houses one or more aquatic animal species;
        ii) a plant growing apparatus which houses one or more plant species growing in an aqueous environment; and
        iii) a biofilter module for receiving a waste stream including solid waste and water from the tank, the biofilter module comprising a solids removal means and a biological waste digestion unit for digesting solids from the solids removal means to produce plant nutrients, wherein the biological waste digestion unit comprises a biological species that at least partially digests solid waste from said solids removal means to plant nutrients, and further wherein the biological digestion unit comprises a plurality of trays which are able to be rotated such that said trays are actively receiving solids from solids removal means when in a receiving position and not receiving solids from the solids removal means in a non-receiving position, and wherein only a subset of the total number of trays are in the receiving position at any time;
    b) transferring solid waste from said tank to said biofilter module, wherein the solid waste contacts the subset of the total number of trays that are in the receiving position;
    c) placing the subset of the total number of trays in the non-receiving position, wherein the subset of the total number of trays no longer receives solid waste;
    d) allowing the solid waste in the subset in the non-receiving position of the total number of trays to be processed to plant nutrients;
    e) returning the subset of the total number of trays in the non-receiving position to the receiving position; and
    f) transferring said plant nutrients from said the subset in the receiving position of the total number of trays within the biofilter module to said plant growing apparatus.

5. A method according to claim 4, wherein the biofilter module receives a waste stream including waste and water from the plant growing apparatus.

6. The method of claim 4, wherein the subset of the total trays in the receiving position also receives water from a nitrification means.

* * * * *